US012600953B2

(12) United States Patent
Spence et al.

(10) Patent No.: US 12,600,953 B2
(45) Date of Patent: Apr. 14, 2026

(54) COMPOSITIONS AND METHOD FOR ESTABLISHING ORGANOID CULTURES FROM CRYOGENICALLY PRESERVED TISSUE

(71) Applicant: The Regents of the University of Michigan, Ann Arbor, MI (US)

(72) Inventors: Jason Spence, Ann Arbor, MI (US); Yu-Hwai Tsai, Ann Arbor, MI (US); Michael Czerwinski, Ann Arbor, MI (US); John Kao, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 752 days.

(21) Appl. No.: 16/634,818

(22) PCT Filed: Jul. 27, 2018

(86) PCT No.: PCT/US2018/044150
§ 371 (c)(1),
(2) Date: Jan. 28, 2020

(87) PCT Pub. No.: WO2019/027834
PCT Pub. Date: Feb. 7, 2019

(65) Prior Publication Data
US 2021/0087532 A1 Mar. 25, 2021

Related U.S. Application Data

(60) Provisional application No. 62/539,240, filed on Jul. 31, 2017.

(51) Int. Cl.
*A01N 1/125* (2025.01)
*A01N 1/162* (2025.01)
*C12N 5/071* (2010.01)

(52) U.S. Cl.
CPC ........... *C12N 5/0679* (2013.01); *A01N 1/125* (2025.01); *A01N 1/162* (2025.01); *C12N 2501/11* (2013.01); *C12N 2501/415* (2013.01); *C12N 2513/00* (2013.01); *C12N 2533/90* (2013.01)

(58) Field of Classification Search
CPC .............. C12N 5/0679; C12N 2501/11; C12N 2501/415; C12N 2513/00; C12N 2533/90; A01N 1/0221; A01N 1/0284
See application file for complete search history.

(56) References Cited

U.S. PATENT DOCUMENTS

2017/0152486 A1 6/2017 Shen et al.

OTHER PUBLICATIONS

Walsh et al ("Drug response in organoids generated from frozen primary tumor tissues;" Scientific Reports 6:18889 Jan. 2016) (Year: 2016).*
Kleinman et al ("Matrigel: Basement membrane matrix with biological activity;" Seminars in Cancer Biology 15 (2005) 378-386). (Year: 2005).*
Lucassen, A. and R. Wheeler, Legal implications of tissue. Ann R Coll Surg Engl, 2010. 92(3): p. 189-92.
Kapp, M.B., Ethical and legal issues in research involving human subjects: do you want a piece of me? J Clin Pathol, 2006. 59(4): p. 335-9.
Spence, J.R., et al., Directed differentiation of human pluripotent stem cells into intestinal tissue in vitro. Nature, 2011. 470(7332): p. 105-9.
Bredenoord, A.L., H. Clevers, and J.A. Knoblich, Human tissues in a dish: The research and ethical implications of organoid technology. Science, 2017. 355(6322).
Miyoshi, H. and T.S. Stappenbeck, In vitro expansion and genetic modification of gastrointestinal stem cells in spheroid culture. Nat Protoc, 2013. 8(12): p. 2471-82.
Noordhoek, J., et al., Intestinal organoids and personalized medicine in cystic fibrosis: a successful patient-oriented research collaboration. Curr Opin Pulm Med, 2016. 22(6): p. 610-6.
Fatehullah, A., S.H. Tan, and N. Barker, Organoids as an in vitro model of human development and disease. Nat Cell Biol, 2016. 18(3): p. 246-54.
Watanabe, K., et al., A Rock inhibitor permits survival of dissociated human embryonic stem cells. Nat Biotechnol, 2007. 25(6): p. 681-6.
Yin, X., et al., Niche-independent high-purity cultures of Lgr5+ intestinal stem cells and their progeny. Nat Methods, 2014. 11(1): p. 106-12.
International Search Report and Written Opinion, International Patent Application No. PCT/US2018/044150, mailed Oct. 3, 2018, 12 pages.
Mahe et al. Establishment of gastrointestinal epithelial organoids. Current Protocols in Mouse Biology, Dec. 2013, vol. 3, Issue 4, pp. 217-240.

* cited by examiner

Primary Examiner — Fereydoun G Sajjadi
Assistant Examiner — Qinhua Gu
(74) Attorney, Agent, or Firm — Casimir Jones, S.C.; Robert A. Goetz

(57) ABSTRACT

The present application is directed to compositions and methods for establishing organoid cultures from cryogenically preserved tissue (e.g., human biopsy tissue), and related methods of use with such established organoid cultures.

8 Claims, 9 Drawing Sheets

Physician extracts
biopsies

Biopsies are cleaned and
placed in a simple freezing media

Cryopreservation

COMPOSITIONS AND METHOD FOR ESTABLISHING ORGANOID CULTURES FROM CRYOGENICALLY PRESERVED TISSUE

CROSS-REFERENCE TO RELATED APPLICATIONS

The present application claims priority to U.S. Provisional Patent Application No. 62/539,240, filed Jul. 31, 2017, hereby incorporated by reference in its entirety.

FIELD OF THE INVENTION

The present application is directed to compositions and methods for establishing organoid cultures from cryogenically preserved tissue (e.g., human biopsy tissue), and related methods of use with such established organoid cultures.

INTRODUCTION

Limited availability of human tissues has hampered understanding of human biology and disease. Many of these limitations are strictly due to inherent ethical issues associated with human tissue research while others come from legal restrictions put in place across the globe (see, e.g., Lucassen, A. and R. Wheeler, Ann R Coll Surg Engl, 2010. 92(3): p. 189-92; Kapp, M. B., J Clin Pathol, 2006. 59(4): p. 335-9). Still another major factor limiting the use of human tissue is the short time of viability and the need to quickly isolate cells for experimentation. This last factor puts a hard limit on the time and place in which any given live tissue sample can be utilized for research. These restraints on time indicate that a given research laboratory must be prepared when a tissue sample becomes available, and must also be relatively geographically close to the source of collection to utilize the sample within the window of viability.

Improved methods for preserving tissue in a manner permitting viable tissue recovery without time constraints are needed. The present invention addresses this need.

SUMMARY OF THE INVENTION

Experiments conducted during the course of developing embodiments for the present invention demonstrated that human biopsies from the GI tract can be cryo-preserved and, upon thawing, can be cultured to establish long-term organoid cultures. This technique proved successful with all GI tissues attempted including the colon and 2 different regions of the small intestine. Given the simplicity of the freezing media and procedure, it is contemplated that this process will be adaptable to biopsies originating from other organs/tissues, and that the major obstacle will be the identification of tissue-specific recovery conditions following thawing. This simple technique for cryo-preservation of adult human tissues will likely prove to be an important resource for clinical and research applications. Frozen tissue samples can now be shipped across the globe, effectively freeing patients, hospitals, clinics, and research, and diagnostics labs from the necessity of geographical proximity. For example, this method of freezing biopsies could be implemented in efforts to better understand GI disorders in developing countries, since frozen biopsies can now be banked and sent to laboratories across the globe for further experimentation. Moreover, healthy autologous patient tissues could also be stored for future therapeutic use in regenerative and/or cellular approaches to treat disease. Moreover, diverse cohorts of human tissue could be more easily centralized in order to generate more robust human research studies on patient-derived organoids.

Accordingly, in certain embodiments, the present invention provides methods of establishing organoid culture from cryogenically preserved tissue, comprising thawing cryogenically preserved cell-containing tissue; washing the thawed cell-containing tissue (e.g., to remove the freezing media); embedding the thawed and washed cell-containing tissue in an extracellular matrix (ECM) or 3-dimensional scaffold (e.g., MATRIGEL®); incubating for approximately 7 days; releasing epithelium from underlying mesenchyme; isolating the released epithelium; embedding the isolated epithelium in extracellular matrix (ECM) or 3-dimensional scaffold (e.g., MATRIGEL®) with anti-apoptotic and pro-proliferative media; and establishing organoid cultures through adding growth media to the isolated epithelium in extracellular matrix (ECM) or 3-dimensional scaffold.

In certain embodiments, the present invention provides methods of establishing organoid culture from cryogenically preserved tissue, comprising thawing cryogenically preserved cell-containing tissue; washing the thawed cell-containing tissue (e.g., to remove the freezing media); releasing epithelium from underlying mesenchyme; isolating the released epithelium; embedding the isolated epithelium in extracellular matrix (ECM) or 3-dimensional scaffold (e.g., MATRIGEL®) with anti-apoptotic and pro-proliferative media; and establishing organoid cultures through adding growth media to the isolated epithelium in extracellular matrix (ECM) or 3-dimensional scaffold.

In certain embodiments, the present invention provides methods of establishing organoid culture from cryogenically preserved tissue, comprising obtaining a cell-containing tissue from an individual; suspending the cell-containing tissue with freezing media; cooling the vial to a temperature of approximately between −80° C. and −196° C. for an amount of time sufficient to cryopreserve the cells or tissue; thawing the cryogenically preserved cell-containing tissue; washing the thawed cell-containing tissue to remove the freezing media; releasing epithelium from underlying mesenchyme; isolating the released epithelium; embedding the isolated epithelium in extracellular matrix (ECM) or 3-dimensional scaffold (e.g., MATRIGEL®) with anti-apoptotic and pro-proliferative media; and establishing organoid cultures through adding growth media to the isolated epithelium in extracellular matrix (ECM) or 3-dimensional scaffold.

In certain embodiments, the present invention provides methods of establishing organoid culture from cryogenically preserved tissue, comprising obtaining a cell-containing tissue from an individual; suspending the cell-containing tissue with freezing media; cooling the vial to a temperature of approximately between −80° C. and −196° C. for an amount of time sufficient to cryopreserve the cells or tissue; thawing the cryogenically preserved cell-containing tissue; washing the thawed cell-containing tissue to remove the freezing media; embedding the thawed and washed cell-containing tissue in extracellular matrix (ECM) or 3-dimensional scaffold (e.g., MATRIGEL®); incubating for approximately 7 days; releasing epithelium from underlying mesenchyme; isolating the released epithelium; embedding the isolated epithelium in extracellular matrix (ECM) or 3-dimensional scaffold (e.g., MATRIGEL®) with anti-apoptotic and pro-proliferative media; and establishing organoid cultures through adding growth media to the isolated epithelium in extracellular matrix (ECM) or 3-dimensional scaffold.

In some embodiments, releasing epithelium from underlying mesenchyme is accomplished with DIASPASE® treatment or EDTA treatment.

In some embodiments, the freezing media comprises DMEM/F12, 10% FBS, and 10% DMSO.

In some embodiments, the growth media comprises Wnt3a, Rspondin1, Noggin, and epidermal growth factor (EGF). In some embodiments, the growth media further comprises one or more of advanced DMEM/F12, GLUTA-MAX™, HEPES, N2 Supplement, B27™ Supplement, Pen/Strep, N-acetylcystine, and Nicotinamide. In some embodiments, the growth media further comprises one or more of TZV, SB431542, CHIR-99021, and Y27632.

In some embodiments, the cell-containing tissue is gastrointestinal tissue. In some embodiments, the cell-containing tissue is from the colon, the distal ileum, the jejunum, the duodenum, and/or the stomach.

BRIEF DESCRIPTION OF DRAWINGS

FIG. 4: Organoids derived from fresh and frozen tissue appear morphologically indistinguishable after passage. Organoids derived of duodenum (Columns A-B), ileum (columns C-D) and colon (columns E-F) have different morphological characteristics when derived of fresh tissue (A1-A4, C1-C4, E1-E4). Duodenum derived organoids grow as smooth cystic structures regardless of whether they originate from fresh or frozen tissue (A1-A4, B1-B4). Organoids from fresh ileum and colon grow with distinct budded morphology while those derived from patient matched frozen tissue (D1-D4, F1-F4) lack these morphological distinctions during the early phases of culture establishment. After the first passage and for the remainder of the

Figure 1:
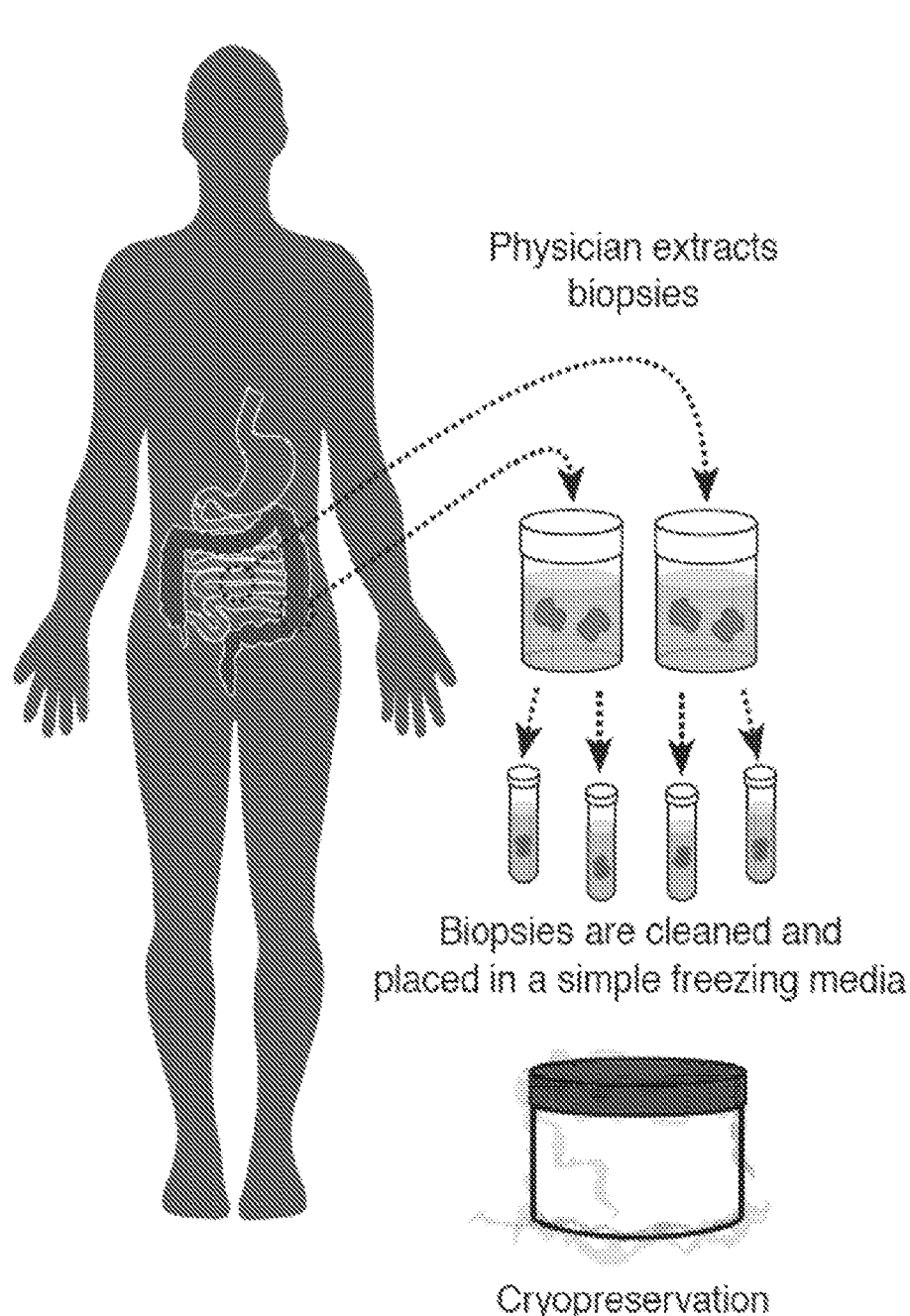
FIG. 1: Schematic of the methods developed that allow successful generation of patient biopsy-derived epithelial organoids following cryopreservation. The process of endoscopic biopsy collection followed by cryo-preservation in a simple freezing medium was accomplished in typical clinical settings with readily available equipment. After cryopreservation, organoid cultures was established using 3 different techniques. Technique 1 (left) utilized a DIASPASE® digestion to isolate crypts from freshly thawed tissue. Technique 2 (middle) adds a step relative to Technique 1 in which the entire biopsy is embedded in MATRI-GEL® and allowed to repair from the freezing process prior to tissue digestion and crypt isolation. Technique 3 (right) is very similar to Technique 1 but uses a gentle EDTA treatment to separate the epithelium from the mesenchyme. All 3 techniques result in pure organoid cultures about 2 weeks after initially thawing the biopsy.
Figure 1:
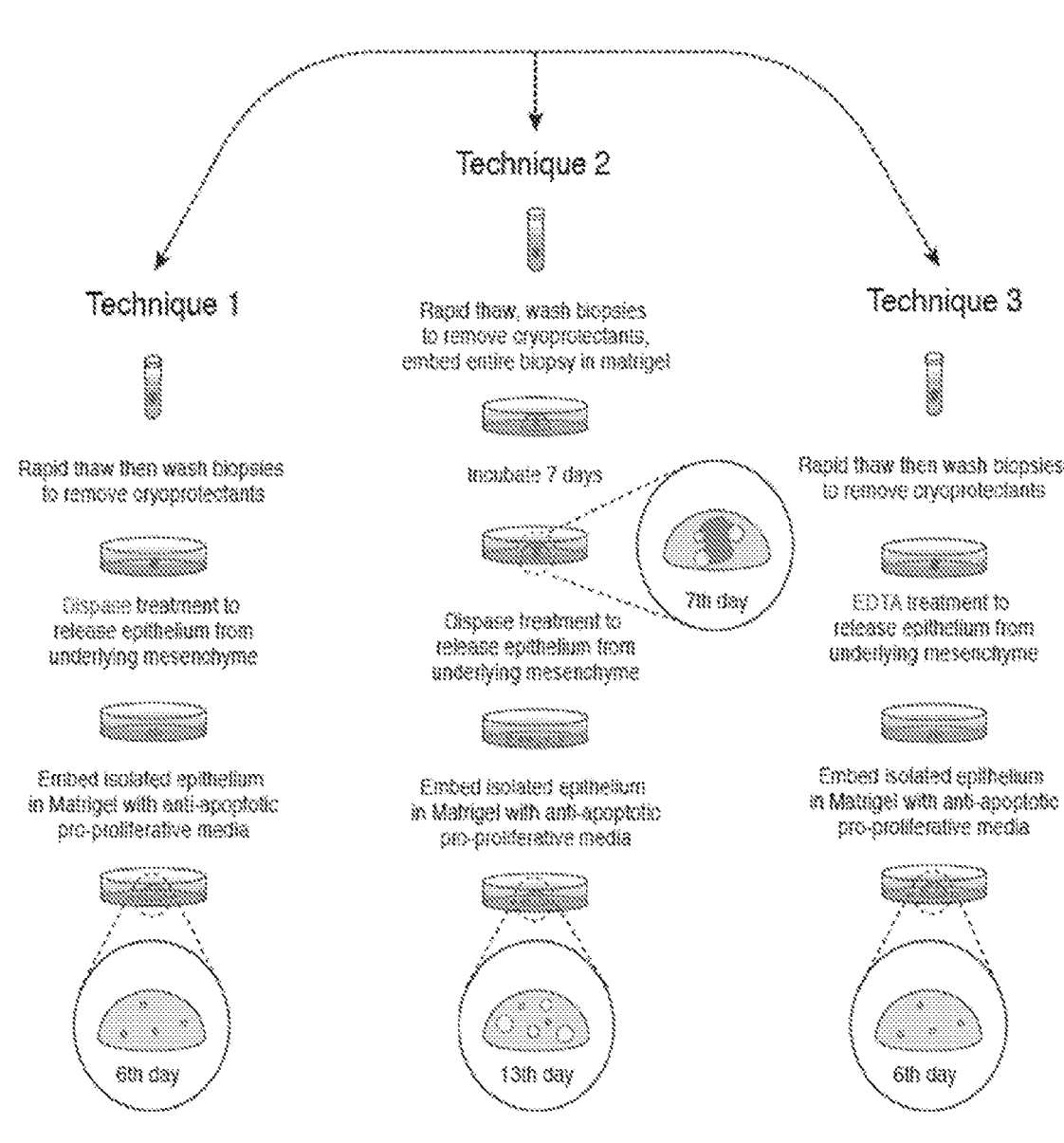

4 observed lifetime of the culture, fresh and frozen organoid morphologies cannot be distinguished (A4-F4).

DEFINITIONS

As used herein, the term "organoid" refers to an 'organ-like' structure that is derived from primary human tissue, which is grown in tissue culture for long periods of time, and which represents some aspects of the native tissue. For example, patient derived organoids are often grown in 3-dimensional cultures and can be comprised of an epithelium only, possessing different epithelial cell types. Alternatively, organoids can be comprised of an epithelium and mesenchymal layer.

DETAILED DESCRIPTION OF THE INVENTION

Human tissue derived gastrointestinal (GI) organoids have revolutionized the study of human organ development and disease (see, e.g., Spence, J. R., et al., Nature, 2011. 470(7332): p. 105-9; Bredenoord, A. L., H. Clevers, and J. A. Knoblich, Science, 2017. 355(6322); Miyoshi, H. and T. S. Stappenbeck, Nat Protoc, 2013. 8(12): p. 2471-82). While organoid research has become more prevalent, the aforementioned limited window of opportunity to use viable tissue is still a major consideration. Moreover, isolation of epithelial cells and subsequent culture of these cells to develop an organoid line is labor and time intensive; limiting the throughput with which new organoid lines can be developed. Moreover, it is not always feasible to prospectively develop organoid lines as part of efforts to develop patient biorepositories to study disease. Drug development, stem cell therapies and personalized medicine approaches are also beginning to use patient-derived organoids to drastically improve the pace of development and broaden the applicability of findings (see, e.g., Noordhoek, J., et al., Curr Opin Pulm Med, 2016. 22(6): p. 610-6; Fatehullah, A., S. H. Tan, and N. Barker, Nat Cell Biol, 2016. 18(3): p. 246-54).

Experiments conducted during the course of developing embodiments for the present invention investigated the identification of practical methods to cryo-preserve live human biopsy tissue, which could then be stored or shipped frozen and later thawed to generate new cultures of gastrointestinal (GI) epithelial organoids. It was found that a simple freezing medium and procedure can be used to cryo-preserve live human gastrointestinal biopsies that, when thawed under specific conditions, can subsequently generate new organoid cultures. It was shown that this technique works with biopsies from 3 different regions of the gastrointestinal tract and produced organoids that appear phenotypically similar to those derived from fresh tissue and with the same efficiency. It is contemplated that such methods will allow an expansion in the scope of biobanking efforts since the relatively simple process of cryo-preservation can be effectively done in the clinic with little to no training required. Frozen tissue can then be stored for future use or shipped to distant laboratories to create new organoid lines for research, patient diagnostics or for regenerative medicine.

Accordingly, the present application is directed to compositions and methods for establishing organoid cultures from cryogenically preserved tissue (e.g., human biopsy tissue), and related methods of use with such established organoid cultures (e.g., personalized medicine uses, development of biobanks of human tissue.

In certain embodiments, disclosed herein are methods of clinical processing and cryopreservation of a cell-containing sample. In some embodiments, the method comprises: obtaining a cell-containing tissue from an individual (e.g., a human individual), optionally dissociating the tissue to form a single cell suspension; suspending the cells or tissue with freezing media; placing the freezing media/cell-containing tissue suspension in a cryopreservation vial; cooling the vial to a temperature of approximately between −80° C. (e.g., −60° C.; −70° C.; −80° C.; −85° C.; −86° C.; −90° C.; or cooler) and −196° C. (e.g., −190° C.; −195° C.; −198° C.; −200° C.; −205° C.; −220° C.; or cooler) for an amount of time sufficient to cryopreserve the cells or tissue (e.g., 1 hour, 2 hours, 10 hours, 20 hours, 1 day, 2 days, 1 week, 1 month, 1 year, 1 decade, etc.).

In certain embodiments, disclosed herein are methods of establishing organoid cultures from cryogenically preserved tissue. In some embodiments, the method comprises thawing (e.g., in a 37° C. water bath) cell-containing tissue cryogenically preserved in a cryopreservation vial; washing the thawed cell-containing tissue to remove the freezing media; releasing epithelium from underlying mesenchyme (e.g., with DIASPASE® treatment) (e.g., with EDTA treatment); isolating the released epithelium; embedding the isolated epithelium in extracellular matrix (ECM) or 3-dimensional scaffold (e.g., MATRIGEL®) with anti-apoptotic and pro-proliferative media; establishing organoid cultures through adding growth media to the isolated epithelium in extracellular matrix (ECM) or 3-dimensional scaffold.

In certain embodiments, disclosed herein are methods of establishing organoid cultures from cryogenically preserved tissue. In some embodiments, the method comprises thawing (e.g., in a 37° C. water bath) cell-containing tissue cryogenically preserved in a cryopreservation vial; washing the thawed cell-containing tissue to remove the freezing media; embedding the thawed and washed cell-containing tissue in extracellular matrix (ECM) or 3-dimensional scaffold (e.g., MATRIGEL®); incubating for approximately 7 days (e.g., 5, 6, 7, 8, 9 days); releasing epithelium from underlying mesenchyme (e.g., with DIASPASE® treatment) (e.g., with EDTA treatment); isolating the released epithelium; embedding the isolated epithelium in extracellular matrix (ECM) or 3-dimensional scaffold (e.g., MATRIGEL®) with anti-apoptotic and pro-proliferative media; establishing organoid cultures through adding growth media to the isolated epithelium in extracellular matrix (ECM) or 3-dimensional scaffold.

Such methods are not limited to a specific formulation for the freezing media. In some embodiments, the freezing media formulation is DMEM/F12, 10% FBS, and 10% DMSO.

Such methods are not limited to a specific formulation for the growth media. In some embodiments, the growth media includes Wnt3a, Rspondin1, Noggin, and EGF. In some embodiments, the growth media further includes one or more of advanced DMEM/F12, GLUTAMAX™, HEPES, N2 Supplement, B27™ Supplement, Pen/Strep, N-acetyl-cystine, and Nicotinamide. In some embodiments, the growth media is further supplemented with one or more of TZV, SB431542, CHIR-99021, and Y27632.

Such methods are not limited to a particular type of cell-containing tissue. In some embodiments, the cell-containing tissue is gastrointestinal tissue. In some embodiments, the cell-containing tissue is from the colon, the distal ileum, the jejunum, the duodenum, and/or the stomach.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes the establishment of organoid culture from cryogenically preserved human biopsy tissue.

Figure 2:
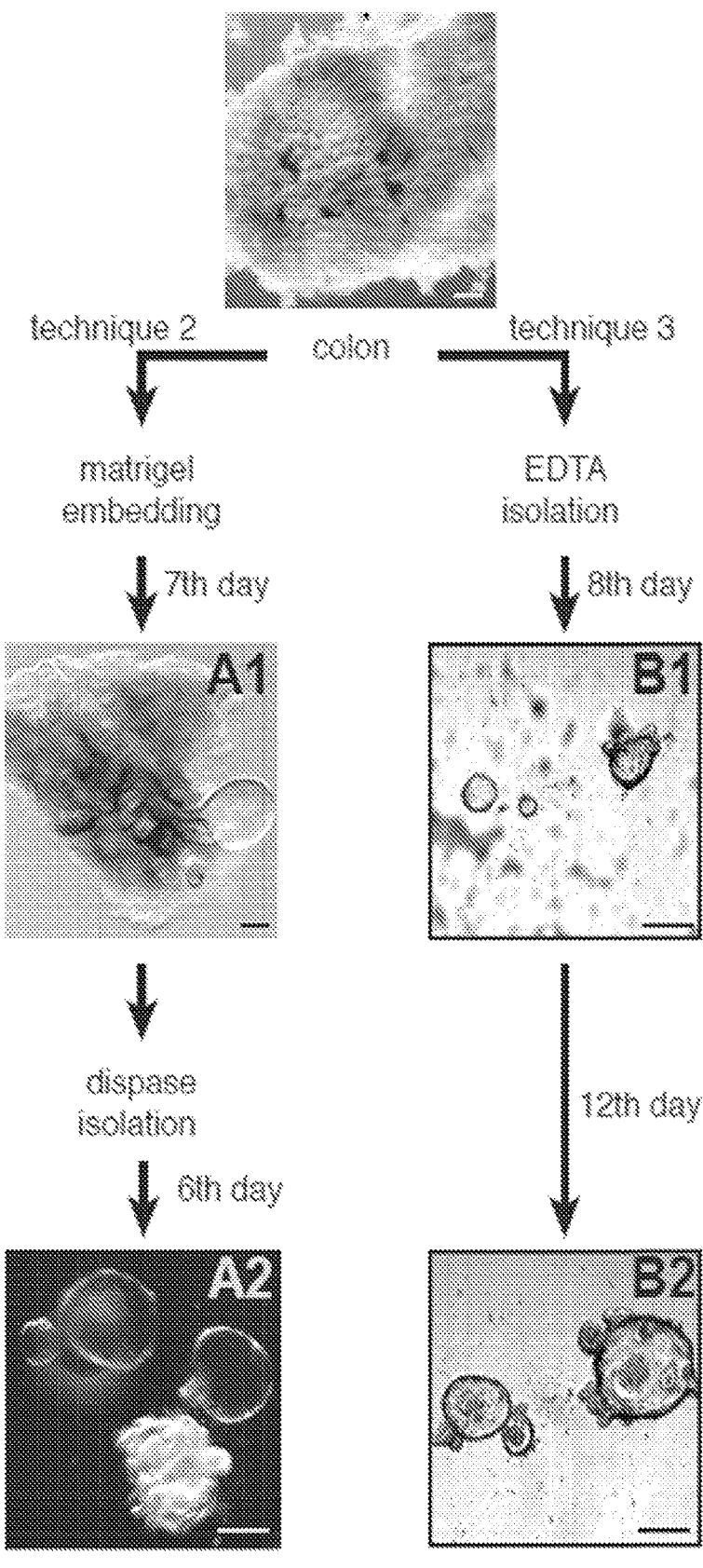
FIG. 2: Schematic demonstrating organoids derived from colonic tissue with Techniques 2 and 3.

In order to freeze gastrointestinal biopsy specimens, endoscopic biopsies were taken with 8 mm² biopsy forceps (average biopsy size 5 mm²), placed into sterile saline solution in the hospital procedure room, and were subsequently transported to the laboratory on ice and were frozen between 30 minutes and 6 hours after samples were collected. Experiments tested two freezing media: 1) a complex medium made up of organoid growth medium (LWRN) supplemented with 10% FBS, 10% DMSO and inhibitors to block apoptosis, Y27632 (1 μM), and to promote stem cell division, CHIR-99021 (4 μM) (see, e.g., Watanabe, K., et al., Nat Biotechnol, 2007. 25 (6): p. 681-6; Yin, X., et al., Nat Methods, 2014. 11 (1): p. 106-12); 2) a simple freezing medium that consisted of DMEM/F12 (Gibco #11330-032) supplemented with 10% FBS and 10% DMSO. To improve diffusion of the freezing media into the tissue, biopsies were cut into 2-3 mm² fragments, which were transferred into a crypreservation vial containing freezing medium. Using a simple laboratory cell freezing container "Mr Frosty" (ThermoFisher #5100-0001), the biopsy fragments were frozen to −80° C. overnight (see detailed methods). While biopsies frozen in complex media produced viable organoid cultures when thawed, there was no appreciable improvement over the simple freezing media. Thus, it was decided to focus on the simple media. Upon thawing the cryopreserved biopsies, three standardized methods were developed that allowed successful separation of the epithelium from the underlying mesenchymal cells and successful establishment of organoid growth (see, FIG. 1). Frozen vials were rapidly thawed in a 37° C. water bath, then washed in "recovery media" containing anti-apoptotic and pro-growth small molecules to remove residual DMSO (FIG. 1). The tissue was then partially digested with Dispase or EDTA to loosen the adhesion between cell layers (FIG. 1, Technique 1 & 3) (see, e.g., Miyoshi, H. and T. S. Stappenbeck, Nat Protoc, 2013. 8 (12): p. 2471-82). For Technique 1, the epithelium was mechanically released from the submucosa by passing it through a pipet. Fragments of epithelium released from the tissue, including visible crypts, were manually collected under a stereomicroscope. For Technique 3, the thawed biopsy was placed into a tube with EDTA, incubated and then shaken vigorously by hand to dislodge the epithelium (see, FIG. 2B). The epithelium was pelleted by gentle centrifugation and was suspended in recovery medium. For both Techniques 1 & 3, the isolated epithelium was embedded in MATRIGEL® where it was cultured for 3 days in recovery media (see, e.g., Yin, X., et al., Nat Methods, 2014. 11 (1): p. 106-12). To determine if omitting the enzymatic digestion enhanced tissue recovery experiments were conducted that also tested a second thawing technique (FIG. 1, Technique 2; FIG. 2, Technique 2). In this case experiments simply thawed the biopsies, washed away the freezing media with recovery media and embedded whole biopsy fragments in MATRIGEL® directly. These cultures were grown in recovery media for 1 week, during which time we observed epithelial expansion (FIG. 2A). These biopsies were then manually removed from the MATRIGEL® and the epithelium was enzymatically dissociated from the tissue in a manner similar to Technique 1 (FIG. 1). It is contemplated that Technique 2 is useful in cases where the initial biopsy is small and loss of tissue during dissection is a concern.

Figure 3:
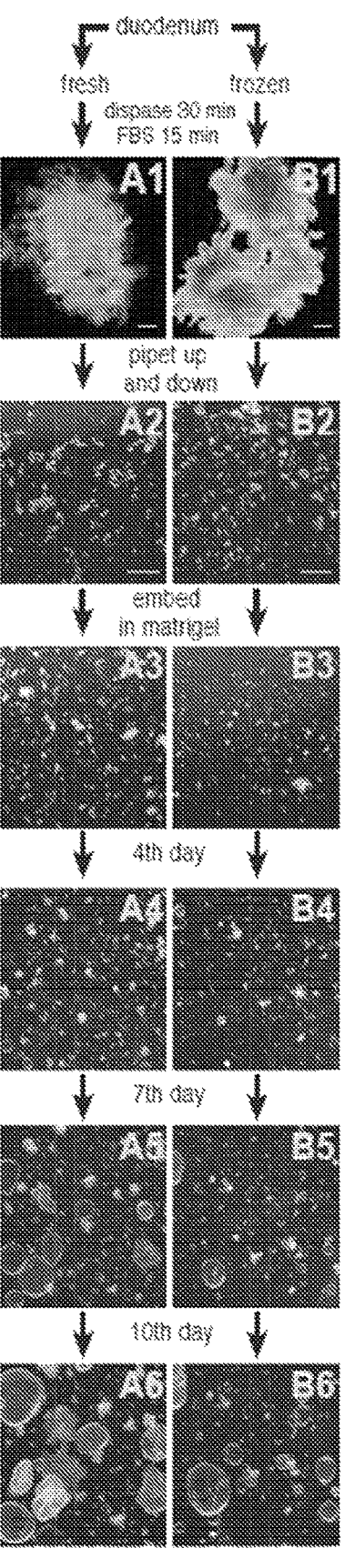
FIG. 3: Organoids derived of frozen tissue have delayed initial growth characteristics. Biopsies from duodenum (Columns A-B), ileum (columns C-D) and colon (columns E-F) can be used to derive intestinal organoids before and after freezing. Epithelial fragments from fresh biopsies (A2, C2, E2) are larger and contain recognizable crypts compared to the small fragments from frozen (B2, D2, F2) samples. Growth kinetics are delayed in cultures established from frozen tissue (B2-B5, D2-D5, F2-F5) relative to fresh tissue (A2-A5, C2-05, E2-E5), but attain normal growth kinetics and size by 10 days in culture (A6-F6).
Figure 3:
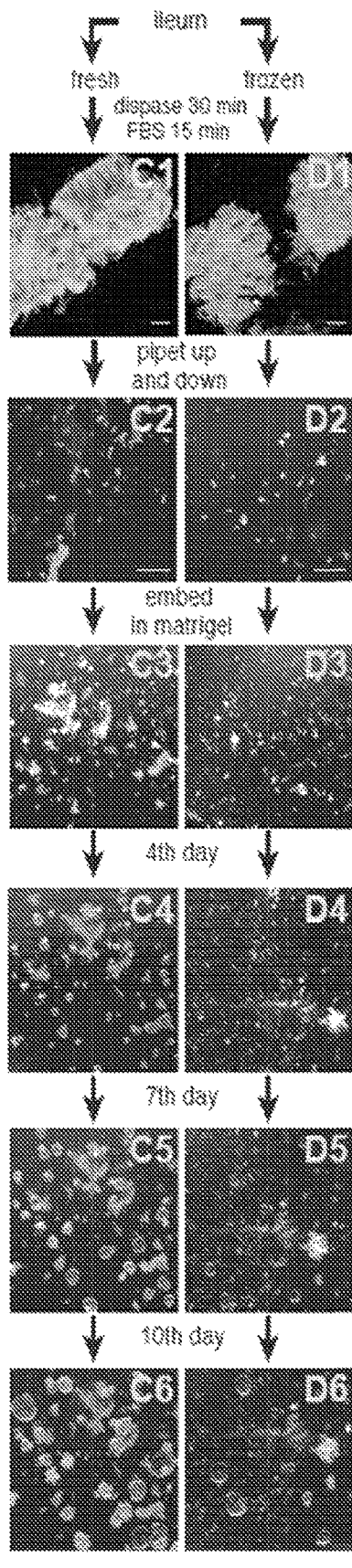
Figure 3:
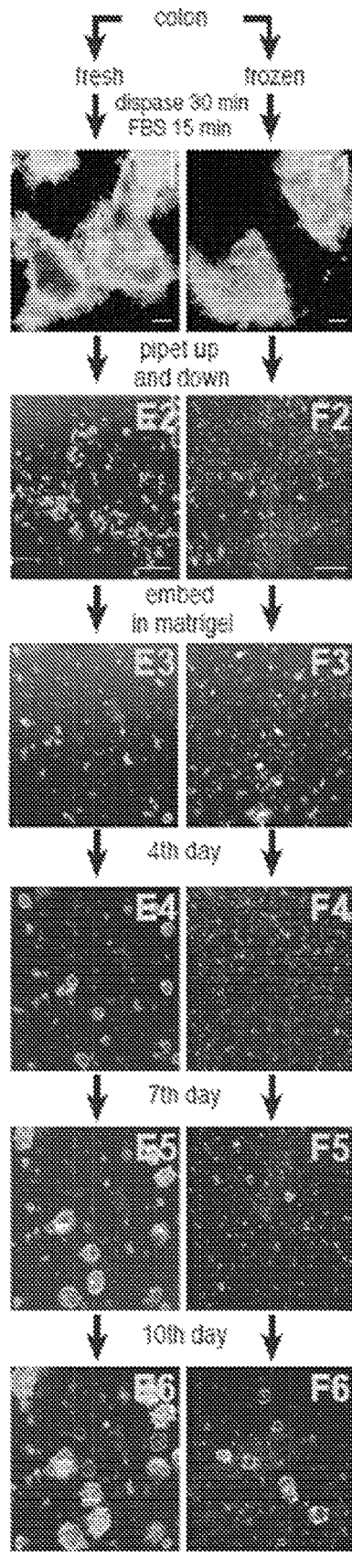
Figure 4:
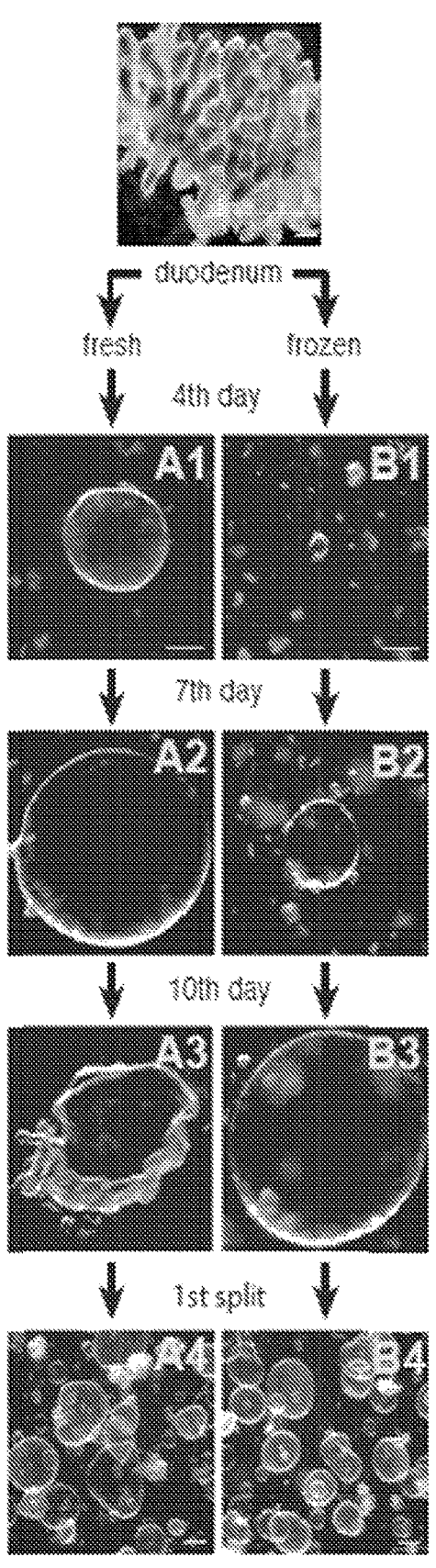
Figure 4:
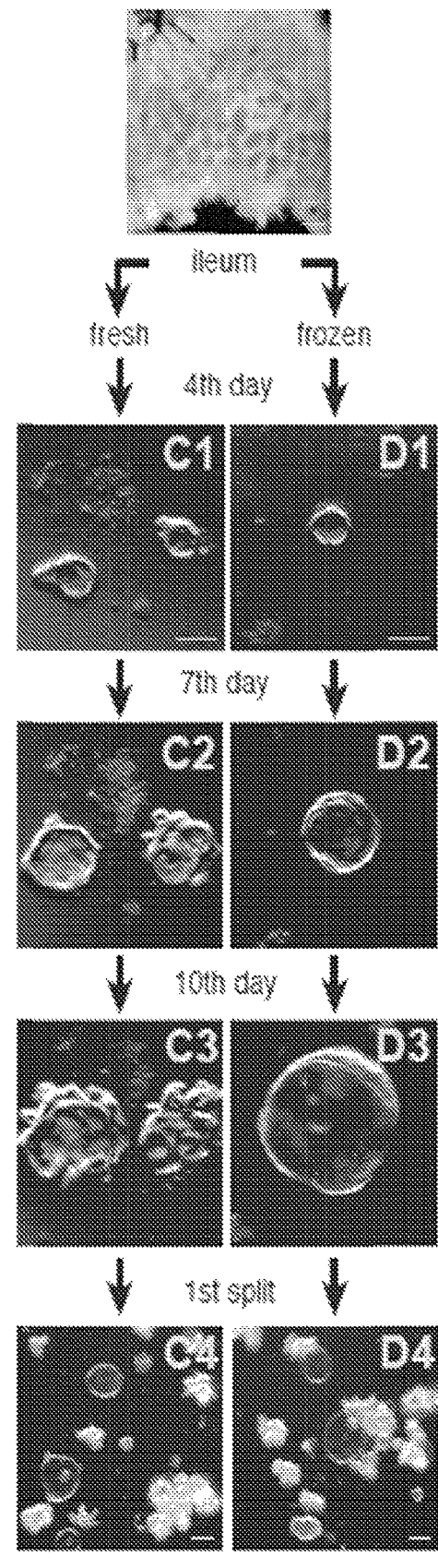
Figure 4:
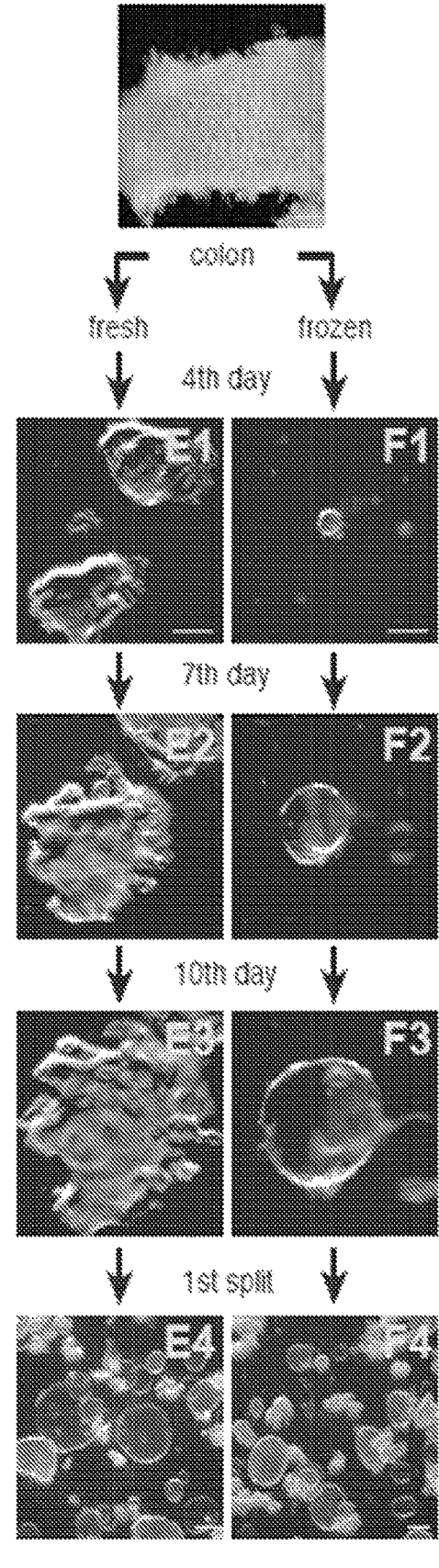

In total, such experiments established patient-matched fresh and frozen biopsy-derived organoid lines, from 3 different regions of the GI tract and from 12 independent patient samples using Techniques 1 & 2, with a 100% success rate (Table 1A; FIG. 3, A1-F1). Experiments generated 3 additional organoid lines from 3 independent patient samples using Technique 3, with a 100% success rate (Table 1B). It was observed that the initial growth of organoids is delayed from frozen samples when compared to freshly isolated epithelium. After enzymatic digestion with Dispase, the resulting fragments of epithelium derived from the frozen samples appear smaller than those from fresh (FIG. 3, A2-F2), resulting in smaller and fewer fragments used in the initial seeding process for organoid cultures (FIG. 3, A3-F3). Frozen tissue derived organoids appear to form smaller and fewer cysts that then appear to expand at a similar rate to those derived from fresh tissue. By 10 days in culture, there are at least some frozen tissue-derived organoids that are equal in size to those derived from matched fresh tissue (FIG. 3, A6-F6). The trend of delayed growth, possibly due to the reduced size of initial epithelial fragments, is consistent across all 3 GI tissue types used in this study (Table 1; FIG. 4, duodenum, ileum and colon).

TABLE 1A

| Patient ID | Patient Age (years) | Patient Sex | GI Region | Successful Enteroids (Fresh) | Successful Enteroids (Frozen) | Days Frozen at −80° C. |
|---|---|---|---|---|---|---|
| 98 | 70 | Female | colon | yes | yes | 3 |
| 99 | 59 | Female | colon | yes | yes | 3 |
| 100 | 67 | Male | colon | yes | yes | 3 |
| 101 | 59 | Female | colon/ileum | yes/yes | yes/yes | 3 & 10 |
| 102 | 61 | Female | colon | yes | yes | 3 & 10 |
| 103 | 63 | Female | colon/ileum | yes/yes | yes/yes | 3 & 10 |
| 104¶ | 51 | Male | colon/ileum | yes/yes | yes/yes | 3 |
| 105¶ | 19 | Male | colon/ileum | yes/yes | yes/yes | 3 |
| 114 | 43 | Male | colon/duodenum | yes/yes | yes/yes | 3 |
| 115 | 46 | Female | duodenum | yes | yes | 3 |
| 116 | 54 | Female | duodenum | yes | yes | 3 |
| 117 | 67 | Female | duodenum | yes | yes | 3 |

Organoid lines generate using Technique 1.

¶Frozen biopsies were also shipped to Baylor College of Medicine, where successful organoid lines were established using technique 1 and/or technique 3.

TABLE 1B

| Patient ID | Patient Age (years) | Patient Sex | GI Region | Successful Enteroids (Fresh) | Successful Enteroids (Frozen) | Days Frozen at −80° C. |
|---|---|---|---|---|---|---|
| 148 | 49 | F | colon | N/A | yes | 4 |
| 151 | 66 | F | colon | N/A | yes | 6 or 13 |
| 150 | 64 | M | colon | N/A | yes | 34 (−80/LN2) |

Organoid lines generated using Technique 3.

Experiments observed that the 3-dimensional morphology of organoids varies depending on the tissue region of origin. In general, the complexity of the organoid increases as the tissue origin moves distally. Duodenum-derived organoids generally grew as smooth spheres/cysts until the culture reached a point where they were ready to be passaged (FIG. 4, A1-B4), Organoids from ileum and colon display considerable budding (FIG. 4, C1-D4, E1-F4), This is true as early as the initial seed culture from fresh tissue, but frozen tissue-derived organoids tended to grow as smooth cystic structures for the first part of culture establishment. After splitting, frozen tissue-derived organoids began budding and were indistinguishable front the fresh tissue derived cultures.

Organoid generation from cryo-preserved biopsies was robust and did not appear to be restricted by patient demographics (Table 1). These patients ranged in age from 19 to 70 years and consisted of both males and females. Experiments were able to isolate epithelium and successfully establish organoid cultures from every patient using Techniques 1 & 2 (n=12) and from 100% of biopsies using Technique 3 (n=3). To ensure that degradation of resident stem cells did not occur over time after freezing, experiments kept a subset of samples frozen at −80° C. or in liquid nitrogen for various times ranging from 1 to 10 days with successful results in each case. To test the idea that frozen biopsies can be shipped long distances and retain their ability to establish organoid cultures, biopsies from 2 patients were frozen at University of Michigan and shipped on dry ice to Baylor College of Medicine. These biopsies were thawed and used to establish successful organoid cultures from both patients (Table 1, Patients 104 and 105). These results indicate that GI stem cells can be isolated and cultured after cryo-storage of biopsies from a broad human demographic.

Example II

This example describes the materials and methods for the experiments described in Example I.

Media Formulations

LWRN Growth Media is produced as previously described (see, e.g., Miyoshi, H. and T. S. Stappenbeck, Nat Protoc, 2013. 8 (12): p. 2471-82). Conditioned media from L-WRN cells containing Wnt3a, Rspondin1, and Noggin, is mixed 1:1 with a 2× basal media comprised of:

Advanced DMEM/F12—214 mL
GLUTAMAX™ (100×, 200 mM)—5 mL
HEPES (100×, 1M)—5 mL
N2 Supplement (100×)—5 mL
B27™ Supplement (50×)—10 mL.
Pen/Strep (100×)—5 mL
N-acetylcystine (500 mM)—1 mL
Nicotinamide (1M)—5 mL.

Recovery Media consists of LWRN Growth Media supplemented with TZV (2.5 µM), SB431542 (100 nM), CHIR-99021 (4 µM), and Y27632 (1 µM). This media is used for initial thawing as well as the first 24 hours of culture to inhibit apoptosis in the thawed cells. After the first 24 hours, Recovery Media minus Y27632 is used for the next 48 hours.

Enteroid Culture

Once established from frozen or fresh tissue, all enteroid cultures were cultured as previously described (see, e.g., Miyoshi, H. and T. S. Stappenbeck, Nat Protoc, 2013. 8(12): p. 2471-82). Media changes occurred every 2 days with LWRN Growth Media.

Biopsy Collection and Cryopreservation

Human tissue biopsies were collected via endoscopy from the colon, distal ileum and duodenum. Biopsies were stored on ice in sterile saline after initial collection and prior to transport to the lab. To remove potential contaminants, all biopsies were washed 3 times with sterile PBS. Large biopsies were then cut into pieces no larger than 3 mm² and resuspended in 1 ml freezing media (DMEM/F12, 10% FBS, 10% DMSO) each in individual cryovials. Slow freezing was accomplished with freezing containers (ThermoFisher #5100-0001) filled with 250 mL isopropanol placed at −80° C. overnight. For long-term storage, frozen biopsies were then moved to liquid nitrogen storage.

Establishment of Enteroid Cultures from Frozen Biopsies

Cryovials containing biopsies were rapidly thawed by submerging the lower half into a 37° C. water bath. Freezing media was then gently removed from thawed biopsies and replaced with recovery media. Biopsies were then transferred to a petri dish and minced into smaller pieces with a sterile scalpel. To separate the epithelium from the underlying cell layers, minced biopsies were then incubated in Dispase (STEMCELL Technologies #07923) for 30 minutes on ice. Dispase was then removed and replaced with 100% FBS for 15 minutes on ice. To mechanically separate the tissue layers, a volume of Advanced DMEM/F12 (Gibco #12634010) equal to the initial volume of FBS was added to the biopsy tissue before vigorously pipetting the mixture several times. Epithelial fragments then settled to the bottom where they were manually collected on a stereoscope by pipet. The epithelium was then washed with ice cold Advanced DMEM/F12 and allowed to settle to the bottom of a 1.5 mL tube. The media was then withdrawn from the loose tissue pellet and replaced with MATRIGEL®. The MATRIGEL® containing the isolated epithelium was then gently mixed to evenly suspend the cells before being pipetted into individual 50 µL droplets in a 24-well plate. The plate containing the droplets was then incubated at 37° C. for 15 minutes to allow the MATRIGEL® to solidify before adding LWRN Growth Media containing TZV (2.5 µM), SB431542 (100 nM), CHIR-99021 (4 µM), and Y27632 (1 µM). After 24 hours, the media was replaced with LWRN growth media containing TZV (2.5 µM), SB431542 (100 nM), and CHIR-99021 (4 µM). After 3 days, cultures were then maintained with LWRN Growth Media replaced every other day.

Example III

This example describes a protocol for epithelial isolation from fresh human (colon, ileum, duodenum) biopsies for organoid (enteroid) generation.

Equipment:
Stereo microscope
Tissue culture hood
Table top centrifuge
CO₂ incubator/37° C.
Dissecting tools Materials:
Human fresh biopsies: colon/ileum/duodenum
Dispose (Corning 40-235)
FBS
PBS without Mg²⁺ and Ca²⁺ (Thermofisher, 10010-023)
Advanced DMEM/F12 Thermofisher, 12634-010)
Basement Membrane Matrigel (Corning 354234)
HEPES (Thermofisher, 15630-080)
Glutamax100× (Thermofisher, 25050-061)
Thiazovivin (Stemgent, 04-0017)

SB431542 (STEM CELL, 72232)
CHIR99021 (STEM CELL, 72304)
Y27632 (STEM CELL, 72304)
N2 Supplement (Thermofisher, 17502-048)
B27 Supplement (Thermofisher, 0080085-SA)
Pen/Strep (Thermofisher, 15140-122)
N-acetylcysteine (Sigma, A9165-5G)
EGF (R&D Systems, 236-EG-200)
Nicotinamide (Sigma, N0636)
LWRN Conditioned Media
24-well culture plate
Growth/Thawing Media for Human Organoids (Enteroids):
  1. Human 2×: basal media (can make 250 mL at a time)

| Component | Amount | Final concentration |
| --- | --- | --- |
| Advanced DMEM/F12 | 214 mL | NA |
| Glutamax (100x-200 mM) | 5 mL | 2X |
| HEPES (100X, 1M) | 5 mL | 2X |
| N2 Supplement (100X) | 5 mL | 2X |
| B27 Supplement (50x) | 10 mL | 2X |
| Pen/Strep (100X) | 5 mL | 2X |
| N-acetylcysteine (500 mM) | 1 mL | 2 mM |
| Nicotinamide (1M) | 5 mL | 20 mM |

2. To make growth media add LWRN conditioned media in a 1:1 mixture with Human 2× basal media and add EGF to a final concentration of 100 ng/mL (this is referred to as LWRN Growth Media)

| Small molecule inhibitors | dilution |
| --- | --- |
| Thiazovivin (TZV) (10 mM) | 1:4000 |
| SB431542 (100 µM) | 1:1000 |
| Y-27632 (10 mM) | 1:1000 |
| CHIR99021 (10 mM) | 1:2500 |

Procedure:
  1. Biopsies obtained from endoscopy can be provided in sterile saline. Take biopsies out of saline and place into a petri dish
  2. Fill dish with ice cold PBS
  3. Cut biopsy tissues into pieces approximately 3 mm$^2$ in the petri dish with a sterile disposable scalpel blade
  4. Transfer tissue into a 6-well TC-plate and incubate in Dispase for 30 minutes on ice
  5. Remove Dispase and incubate in 100% PBS for 15 minutes on ice
  6. Add equal volume of Advanced DMEM/F12
  7. Pipet up and down with pipette to break tissues
  8. Pick out epithelium that sinks to the bottom under a dissecting microscope in sterile conditions
  9. Put the epithelium in a clean petri dish with fresh cold Advanced DMEM/F12 to rinse the epithelium
  10. Collect the epithelium in a 1.5 ML Eppendorf tube and let the epithelium settle to the bottom of the tube on ice
  11. Withdraw the media
  12. Add Matrigel to the tube and mix with epithelium
  13. Plate the Matrigel with epithelium in droplets onto the 24-well plate
  14. Allow Matrigel to set up for 15 minutes
  15. Add 500 µL media to each well
  16. Feed the cultures daily for the first 3 days with LWRN Growth Media with TZV, SB431542 and CHIR (4 µM) [and add Y27632 (10 µM) on the 1st day]
  17. After 3 days, feed very other day with LWRN Growth Media
  18. It may take 1 weeks to establish enteroids Example IV This example describes a protocol for epithelial isolation from fresh human (colon, ileum, duodenum) biopsies for organoid (enteroid) generation.
Equipment:
  Inverted light microscope
  Tissue culture hood
  Table top centrifuge
  $CO_2$ incubator/37° C.
  Dissecting tools
Materials:
  Human frozen biopsies: colon/ileum
  Dispase (Corning 40-235)
  FBS
  PBS without $Mg^{2+}$ and $Ca^{2+}$ (Thermofisher, 10010-023)
  Advanced DMEM/F12 (Thermofisher, 12634-010)
  Basement Membrane Matrigel (Corning 354234)
  HEPES (Thermofisher, 15630-080)
  Glutamax100× (Thermofisher, 25050-061)
  Thiazovivin (Stemgent, 04-0017)
  SB431542 (STEM CELL, 72232)
  CHIR99021 (STEM CELL, 72052)
  Y27632 (STEM CELL, 72304)
  N2 Supplement (Thermofisher, 17502-048)
  B27 Supplement (Thermofisher, 0080085-SA)
  Pen/Strep (Thermofisher, 15140-122)
  N-acetylcysteine (Sigma, A9165-5G)
  EGF (R&D Systems, 236-EG-200)
  Nicotinamide (Sigma, N0636)
  LWRN Conditioned Media
  24-well culture plate
Freezing Media:
  80% DMEM (Thermofisher, 11330-032)
  10% FBS
  10% DMSO (SIGMA, D8418)
Growth/Thawing (Recover) Media for Human Organoids (Enteroids):
  3. Human 2×: basal media (can make 250 mL at a time)

| Component | Amount | Final concentration |
| --- | --- | --- |
| Advanced DMEM/F12 | 214 mL | NA |
| Glutamax (100X-200 mM) | 5 mL | 2X |
| HEPES (100x, 1M) | 5 mL | 2X |
| N2 Supplement (100X) | 5 mL | 2X |
| B27 Supplement (50x) | 10 mL | 2X |
| Pen/Strep (100X) | 5 mL | 2x |
| N-acetylcyteine (500 mM) | 1 mL | 2 mM |
| Nicotinamide (1M) | 5 mL | 20 mM |

4. To make growth media add LWRN conditioned media in a 1:1 mixture with Human 2× basal media and add GF; to a final concentration of 100 ng/mL (this is referred to as LWRN Complete media).
  5. To make thawing/recovery media, add the following to the growth media.

| Cell death inhibitors | dilution |
| --- | --- |
| Tiazovivin (TZV) (10 mM) | 1:4000 |
| Sb431542 (100 µM) | 1:1000 |
| CHIR99021 (10 mM) | 1:2500 |

Freeze Human Biopsies:

1. Biopsies obtained from endoscopy are provided in sterile saline. Take biopsies out of saline and place into a petri dish
2. Fill dish with ice cold PBS
3. Aspirate PBS and replace with ice cold freezing media
4. Cut biopsy tissues into pieces approximately 3 $mm^2$ in the petri dish with a sterile disposable #10 scalpel blade
5. Use a cut p1000 pipette to transfer tissues into cryogenic tubes with 1 mL freezing media.
6. Transfer cryogenic tubes into Mr. Frosty and store at −80° C.

Procedure:

19. Take tissues out of Mr. Frosty. Thaw tissues by placing, bottom part of tube in a 37° C. water bath and agitate back and forth by hand for rapid thawing. Do not submerge cap in water bath.
20. Once Thawed, spray tube down with 70% ethanol, and move to TC hood. Immediately place tissues and freezing media in a petri dish with ice cold recovery media
21. Cut tissue into smaller pieces with scalpel
22. Transfer tissue into a 6-well TC-plate and incubate in 1-2 mLs Dispase for 30 minutes on ice
23. Remove Dispase and incubate in 2-4 mLs 100% FBS for 15 minutes on ice
24. Add equal volume of Advanced DMEM/F12
25. Pipet up and down with pipette to break tissues
26. Pick out epithelium that sinks to the bottom under a dissecting microscope in sterile conditions
27. Put the epithelium in a clean petri dish with fresh cold Advanced DMEM/F12 to rinse the epithelium
28. Collect the epithelium in a 1.5 mL Eppendorf tube and let the epithelium settle to the bottom of the tube on ice
29. Withdraw the media
30. Add Matrigel to the tube and mix of epithelium
31. Plate the Matrigel with epithelium in droplets onto the 24-well plate
32. Allow Matrigel to set up for 15 minutes
33. Add 500 µL recovery media to each well
34. Feed the cultures daily for the first 3 days with recovery media [supplemented with Y27632 (10 µM) on the $1^{st}$ day only]
35. After 3 days, feed very other day with LWRN growth media
36. It may take 1 to 2 weeks to establish enteroids

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of establishing organoid culture from cryogenically preserved tissue, comprising:
   obtaining a cell-containing tissue from an individual, wherein the cell-containing tissue is a whole tissue biopsy comprising epithelial tissue comprising crypt cell, stem cells, and underlying mesenchyme;
   suspending the cell-containing tissue with freezing media in a vial;
   cooling the vial to a temperature of approximately between −80° C. and −196° C. for an amount of time sufficient to cryopreserve the cells or tissue;
   thawing the cryogenically preserved cell-containing tissue;
   washing the thawed cell-containing tissue to remove the freezing media;
   embedding the thawed and washed cell-containing tissue in an extracellular-matrix (ECM);
   incubating the embedded cell-containing tissue for about five to nine days to permit post-thaw tissue repair and recovery of epithelium;
   releasing epithelium from underlying mesenchyme;
   isolating the released epithelium;
   embedding the isolated epithelium in ECM with a recovery medium comprising thiazovivin (TZV), SB431542, Y-27632, and CHIR-99021, wherein Y-27632 is present only during an initial twenty-four-hour period following embedding; and
   establishing organoid cultures through adding growth media to the isolated epithelium in extracellular matrix (ECM) following exposure to the recovery medium, wherein the established organoid cultures are capable of expansion beyond 10 days from initiation of organoid culture establishment, wherein the growth medium comprises Wnt3a, Rspondin1, Noggin, and EGF, and one or more of: thiazovivin (TZV), SB431542, and CHIR-99021.
2. The method of claim 1, wherein releasing epithelium from underlying mesenchyme is accomplished with dispase treatment or EDTA treatment.
3. The method of claim 1, wherein the freezing media comprises DMEM/F12, 10% FBS, and 10% DMSO.
4. The method of claim 1, wherein the growth media further comprises one or more of
   advanced DMEM/F12,
   L-Alanyl-L-glutamine,
   HEPES,
   N2 Supplement,
   a supplement comprising: biotin, DL alpha tocopherol acetate, DL alpha-tocopherol, vitamin A, BSA, catalase, human recombinant insulin, human transferrin, superoxide dismutase, corticosterone, D-galactase, ethanolamine HCl, glutathione, L-carnitine HCl, linoleic acid, linolenic acid, prograsterone, putrescine, sodium selenite, and triodo-I-thyronine,
   Pen/Strep,
   N-acetylcystine, and
   Nicotinamide.
5. The method of claim 1, wherein the growth media further comprises Y27632.
6. The method of claim 1, wherein the cell-containing tissue is gastrointestinal tissue.

7. The method of claim 1, wherein the cell-containing tissue is from the colon, the distal ileum, the jejunum, the duodenum, and/or the stomach.

8. The method of claim 1, wherein the extracellular matrix (ECM) comprises laminin, nidogen, collagen, heparan sulfate proteoglycans, EGF and TGF-β.

\* \* \* \* \*